United States Patent [19]
Voultoury et al.

[11] Patent Number: 5,643,583
[45] Date of Patent: Jul. 1, 1997

[54] COSMETIC OR PHARMACEUTICAL COMPOSITION FOR TOPICAL USE

[75] Inventors: Robert Voultoury, Antony; Anne-Marie Scott, Noyon, both of France

[73] Assignee: Laboratoires de Biologie Vegetale Yves Rocher, La Gacilly, France

[21] Appl. No.: 426,954

[22] Filed: Apr. 24, 1995

[30] Foreign Application Priority Data

May 2, 1994 [FR] France .................................. 94 05320

[51] Int. Cl.$^6$ ....................................................... A61K 7/48
[52] U.S. Cl. .................. 424/401; 424/195.1; 424/450; 514/844; 514/846; 514/847
[58] Field of Search ........................... 424/401, 195.1, 424/450; 514/844, 846, 847

[56] References Cited

U.S. PATENT DOCUMENTS 4,892,727  1/1990  Grollier .................................. 424/69

OTHER PUBLICATIONS

Tzen et al in The Journal of Cell Biology vol. 117, 327–335 (1992).

*Primary Examiner*—Jyothsna Venkat
*Attorney, Agent, or Firm*—Young & Thompson

[57] ABSTRACT

The invention relates to a cosmetic or pharmaceutical composition for topical use, comprising lipid vesicles obtained by crushing seeds of oleaginous plants, emulsification in an aqueous phase and filtration.

3 Claims, No Drawings

COSMETIC OR PHARMACEUTICAL COMPOSITION FOR TOPICAL USE

The present invention relates to cosmetic compositions and pharmaceutical compositions for topical use, comprising lipid vesicles.

The present invention relates more specifically to compositions of this type comprising lipid vesicles obtained from seeds of oleaginous plants.

In the seeds of oleaginous plants, the oil (essentially triglycerols) is present in the form of oily bodies which can vary in diameter from 0.1 to 10 micrometres, and which comprise a central core of oil surrounded by a covering consisting of proteins (oleosins) and of phospholipids (J. Tzen et al., J. Cell. Bio, 117,327, 1992).

These oily bodies may be extracted from the oleaginous plants from which they originate by crushing the seeds of oleaginous plants, emulsification in an aqueous phase and filtration.

The present invention is directed towards using these oily bodies for the manufacture of cosmetic and/or pharmaceutical compositions for topical use.

The subject of the present invention is consequently a cosmetic or pharmaceutical composition for topical use, comprising lipid vesicles obtained by crushing seeds of oleaginous plants, emulsification in an aqueous phase and filtration.

In an advantageous form of the invention, instead of incorporating in the compositions the emulsion as obtained after filtration, the lipid vesicles are incorporated in the compositions in the form of a concentrate (having the appearance of a cream) obtained by centrifugation of the emulsion.

In general, the concentrate of lipid vesicles may be incorporated in an aqueous phase in amounts which can represent up to 30% by weight of the composition.

As examples of seeds of oleaginous plants, soya bean, pistachio, macadamia, sunflower, rape, groundnut, almond, hazelnut, sesame, borage, wheat germ and jojoba seeds may be mentioned. It is preferable to use seeds having a high oil content (pistachio, macadamia, groundnut, jojoba, hazelnut).

Stabilization of the emulsions or concentrates may be obtained, in particular, using the following techniques:
Bacteriological stabilization
  heat treatment of the seeds (cooking for 1 hour or longer at a temperature not exceeding 50° C.);
  irradiation of the seeds at 0 to 10 kGy;
  UHT treatment of the emulsion of oily bodies (after filtration and before the centrifugation): 120° C.×5 seconds;
  optional addition, either to the emulsification water or to the aqueous phase of dilution of the concentrate, of preservatives, and for example:

| | |
|---|---|
| • para-benzoic acid esters: | 0 to 5% by weight, |
| • Na$_4$ EDTA: | 0 to 0.1% by weight |
| • sorbic acid: | 0 to 0.5% |
| • imidazolidinylurea: | 0 to 0.5% by weight |
| • sodium dehydroacetate: | 0 to 0.5% by weight |
| • sodium sulphite: | 0 to 0.5% by weight |

Physical stabilization of the compositions

With the minimum of addition of chemical constituents to the aqueous phase of dilution of the concentrates, it is possible to achieve a good stability of the final compositions by adjusting the zeta potential of the particles.

The addition of relevant components will hence be determined as a result of this technique.

Among these components, there may be mentioned:

| | |
|---|---|
| sodium chloride | 0 to 2% by weight |
| citric acid | 0 to 2% by weight |
| hydrolysed pectin | 0 to 1% by weight |
| phosphate buffers | 0 to 1% by weight |

These compositions according to the invention can comprise, in addition, thickeners such as:

| | |
|---|---|
| polyacrylic acids | 0 to 1% by weight |
| xanthan gum | 0 to 1% by weight |
| scleran gum | 0 to 1% by weight |
| bentone and derivatives | 0 to 2% by weight |
| polyacrylamide and derivatives | 0 to 2% by weight |
| carob and/or carrageenans | 0 to 2% by weight |

The compositions according to the invention can, in addition, contain colorants and perfumes.

These compositions according to the invention are equivalent to existing cosmetic compositions, but they have the following advantages relative to these latter:

no synthetic and exogenous emulsifying system, resulting in better skin tolerance;

oleosins possess epitopes of configurations similar to those of the apoproteins of animal lipoproteins. They can hence be recognized by the skin lipases.

The compositions according to the invention can hence lay claim—through their biological similarity—to a better substantivity than that of the existing cosmetic compositions based on synthetic emulsifiers.

Examples illustrating the invention will be given below.

APPLICATION EXAMPLES

Example 1

Face Milk

Macadamia seeds, previously stabilized from a microbiological standpoint, are ground using an impeller breaker.

90 parts of water, with or without the addition of preservatives and antioxidants, are added to 10 parts of the ground preparation. Moderate stirring is maintained for half an hour at a temperature not exceeding 35° C.

The above emulsion (milk) is then filtered using frontal filtration (200-micron cartridge) with a rinsing device, so as to remove the plant pulp.

The emulsion filtered in this way may then be concentrated by centrifugation. A dairy machine is preferred for this operation.

The concentrate (cream) obtained possesses a percentage fat content of the order of 60% by weight. This concentrate may then be diluted, thickened and perfumed to form the following composition:

| | |
|---|---|
| concentrate | 15% to 30% by weight |
| xanthan gum | 1 to 2% by weight |
| perfume | 0.1 to 0.5% by weight |
| preservatives | qs |
| water | qs 100% by weight |

Example 2

Preparation of a Night Cream

The concentrate prepared in Example 1 may be used to manufacture the following composition:

| | |
|---|---|
| concentrate | 20 to 30% by weight |
| glycerol | 2 to 5.0% by weight |
| xanthan gum | 1 to 2.0% by weight |
| polyacrylamide | 5 to 10% by weight |
| perfume | 0.1 to 0.5% by weight |
| preservatives | qs |
| water | qs 100% by weight |

What is claimed is:

1. A cosmetic or pharmaceutical composition for topical use, comprising, in an appropriate base for topical use, an effective amount of lipid vesicles obtained by:
   a. crushing seeds of oleaginous plants to obtain ground seeds, said seeds being selected from the group consisting of soya bean, pistachio, macadamia, sunflower, rape, groundnut, almond, hazelnut, sesame, borage, wheat germ and jojoba seeds,
   b. adding an aqueous phase to said ground seeds and stirring to obtain an emulsion
   c. filtering said emulsion, and
   d. centrifuging said emulsion to form a concentrate of said lipid vesicles, said composition comprising, in an aqueous phase, up to 30% by weight of said concentrate.

2. A cosmetic composition for topical use comprising, in an appropriate cosmetic base, an effective amount of lipid vesicles obtained by:
   a. crushing seeds of oleaginous plants to obtain ground seeds, said seeds being selected from the group consisting of soya bean, pistachio, macadamia, sunflower, rape, groundnut, almond, hazelnut, sesame, borage, wheat germ and jojoba seeds,
   b. adding an aqueous phase to said ground seeds and stirring to obtain an emulsion
   c. filtering said emulsion, and
   d. centrifuging said emulsion to form a concentrate of said lipid vesicles, said composition comprising, in an aqueous phase, up to 30% by weight of said concentrate.

3. A process for the cosmetic treatment of the skin which comprises applying to the skin composition containing an effective amount of lipid vesicles obtained by:
   a. Crushing seeds of oleaginous plants to obtain ground seeds, said seeds being selected from the group consisting of soya bean, pistachio, macadamia, sunflower, rape, groundnut, almond, hazelnut, sesame, borage, wheat germ and jojoba seeds,
   b. adding an aqueous phase to said ground seeds and stirring to obtain an emulsion,
   c. filtering said emulsion, and
   d. centrifuging said emulsion to form a concentrate of aid lipid vesicles, said composition comprising, in an aqueous phase, up to 30% by weight of said concentrate.

* * * * *